United States Patent [19]

Tang et al.

[11] Patent Number: 5,248,786
[45] Date of Patent: Sep. 28, 1993

[54] PROCESS FOR PREPARATION OF 1H-PYRAZOLO (1,5-B) (1,2,4) TRIAZOLE COUPLERS AND INTERMEDIATE COMPOUNDS EMPLOYED IN THE PROCESS

[75] Inventors: Ping-Wah Tang; Terrence C. Mungal, both of Rochester, N.Y.

[73] Assignee: Eastman Kodak Company, Rochester, N.Y.

[21] Appl. No.: 841,484

[22] Filed: Feb. 26, 1992

[51] Int. Cl.⁵ .................. C07D 487/04; C07D 331/06; G03C 7/38
[52] U.S. Cl. .............. 548/369.1; 548/262.4; 548/367.4
[58] Field of Search .................. 548/262.4, 369, 369.1, 548/367.4

[56] References Cited

U.S. PATENT DOCUMENTS

| | | | |
|---|---|---|---|
| 4,540,654 | 9/1985 | Sato et al. | 548/262.4 X |
| 4,621,046 | 11/1986 | Sato et al. | 548/262.4 X |
| 4,705,863 | 11/1987 | Sato et al. | 548/262.4 |

FOREIGN PATENT DOCUMENTS

| | | | |
|---|---|---|---|
| 0119860 | 9/1984 | European Pat. Off. | 548/262.4 |
| 61-261738 | 11/1986 | Japan | 548/262.4 |
| 1-025765 | 1/1989 | Japan | 548/262.4 |
| 2-149582 | 6/1990 | Japan | 548/262.4 |

*Primary Examiner*—Floyd D. Higel
*Attorney, Agent, or Firm*—Wegner, Cantor, Mueller & Player

[57] ABSTRACT

A process of preparing 1H-pyrazolo [1,5-b][1,2,4] triazole compounds represented by formula (I):

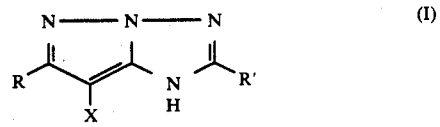

wherein R and R' are independently hydrogen or a substituent and X is hydrogen or a coupling-off group, comprises subjecting a compound of formula (II)

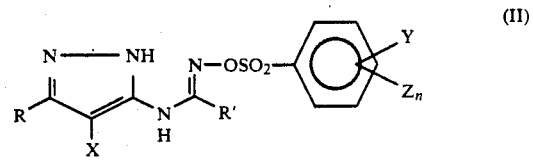

wherein Y and Z are each substituent groups and n is 0, 1 or 2, to a cyclization reaction.

8 Claims, No Drawings

PROCESS FOR PREPARATION OF 1H-PYRAZOLO (1,5-B) (1,2,4) TRIAZOLE COUPLERS AND INTERMEDIATE COMPOUNDS EMPLOYED IN THE PROCESS

BACKGROUND OF THE INVENTION

The present invention relates to a process of preparing 1H-pyrazolo [1,5-b][1,24] triazole compounds represented by formula (I):

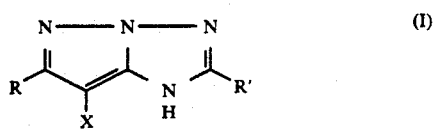

Formula (I) includes pyrazolotriazole compounds which are useful as dye-forming 1H-pyrazolo [1,5-b][1,24] triazole couplers employed in photographic silver halide materials, wherein R and R' are independently hydrogen or coupler substituents known in the photographic art which do not adversely affect the desired properties of the coupler, and X is hydrogen or a coupling-off group known in the photographic art. Such couplers are described in European Patent 177,765 and U.S. Pat. No. 4,450,654, for example. Additionally, formula (I) includes compounds wherein R or R' is a reactive group which can be converted to the coupler substituent, thereby providing a dye-forming 1H-pyrazolo [1,5-b][1,2,4] triazole coupler.

Additionally, the present invention relates to intermediate compounds useful in the process. The intermediates are represented by the formula (II):

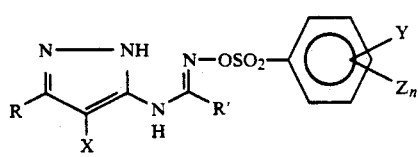

wherein: R, R' and X are as defined for formula (I); Y and Z are each independently a substituent group which has a Hammett sigma value of at least 0.05 ($''_{m,p} \geq 0.05$); and n is 0, 1 or 2.

The

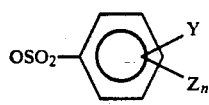

moiety is formula (II) is a leaving group, such that when the compound (II) is subjected to a cyclization reaction according to the process of the present invention, a compound of formula (I) is formed.

Japanese kokai 01-025,765, describes amidoximes having a leaving group of the formula:

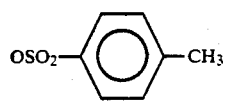

However, the process disclosed in the kokai for formation of pyrazolotriazole compounds is complicated and entails considerable difficulties, involving a number of separation and purification steps for both intermediates and final products. Additionally, the process results in unsatisfactory by-products and low yields.

On the other hand, the intermediates of formula (II) provide a more efficient cyclization for the production of compounds of formula (I). Additionally, the process according to the present invention requires relatively fewer and simpler separation and purification steps.

SUMMARY OF THE INVENTION

In one aspect, the present invention relates to intermediate compounds of formula (II):

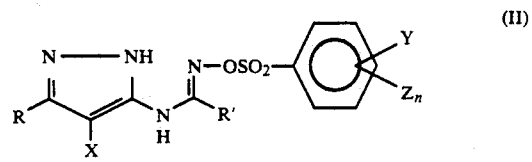

In another embodiment, the present invention relates to a process for the production of 1H-pyrazolo [1,5-b][1,24] triazole compounds of formula (I) wherein compounds of formula (II) are subjected to a cyclization reaction to obtain the compounds of formula (I) according to the following general reaction scheme A:

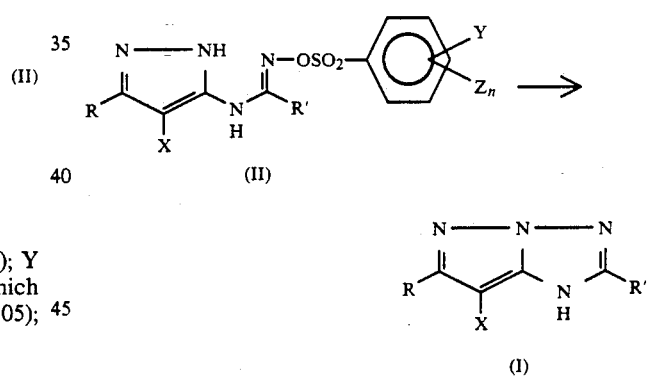

According to another embodiment, the present invention relates to the production of 1H-pyrazolo [1,5b][1,2,4] triazole compounds of formula (I) from compound (II), wherein compound (II) is produced by the following general reaction scheme B:

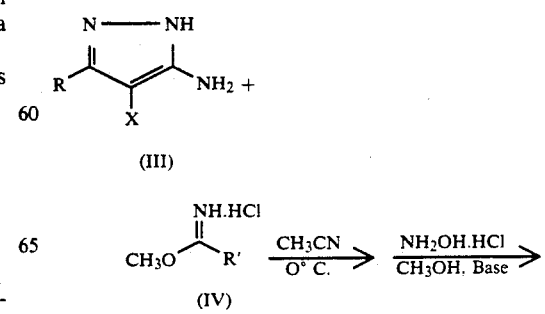

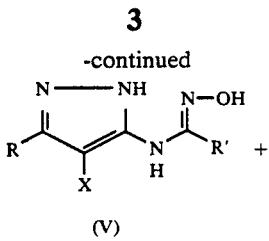

(V)

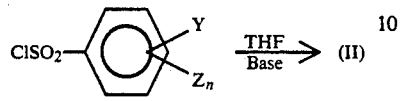

In formulae (III), (IV), (V) and (VI), R, R', X, Y, Z and n are defined above.

DESCRIPTION OF THE PREFERRED EMBODIMENTS

In the above formulae, X is hydrogen or a coupling-off group known in the art. Coupling-off groups are known to those skilled in the art. Such groups can determine the equivalency of the coupler, can modify the reactivity of the coupler, or can advantageously affect the layer in which the coupler is coated or other layers in the element by performing, after release from the coupler, such functions as development inhibition, development acceleration, bleach inhibition, bleach acceleration, color correction, and the like. Representative classes of coupling-off groups include halogen, particularly chlorine, bromine, or fluorine, alkoxy, aryloxy, heterocyclyloxy, heterocyclic, such as hydantoin and pyrazolo groups, sulfonyloxy, acyloxy, carbonamido, imido, acyl, heterocyclicimido, thiocyano, alkylthio, arylthio, heterocyclylthio, sulfonamido, phosphonyloxy and arylazo. They are described in, for example, U.S. Pat. Nos. 2,355,169; 3,227,551; 3,432,521; 3,476,563; 3,617,291; 3,880,661; 4,052,212 and 4,134,766; and in U.K. patents and published application numbers 1,466,728; 1,531,927; 1,533,039; 2,006,755A and 2,017,704A; the disclosures of which are incorporated herein by reference.

Examples of specific coupling-off groups are

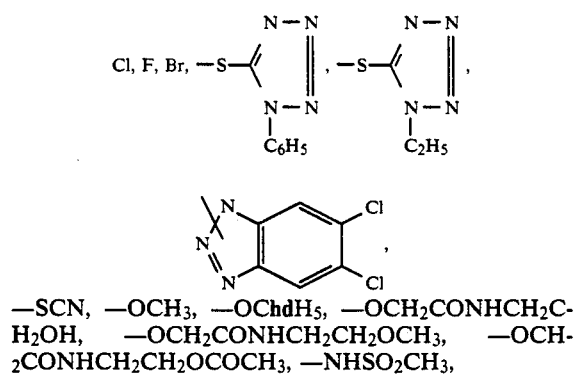

—SCN, —OCH$_3$, —OC$_6$H$_5$, —OCH$_2$CONHCH$_2$CH$_2$OH, —OCH$_2$CONHCH$_2$CH$_2$OCH$_3$, —OCH$_2$CONHCH$_2$CH$_2$OCOCH$_3$, —NHSO$_2$CH$_3$,

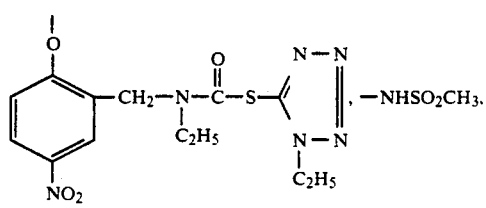

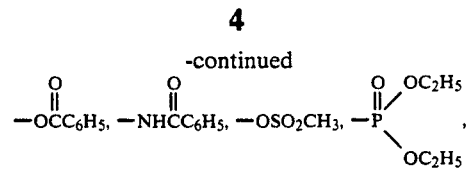

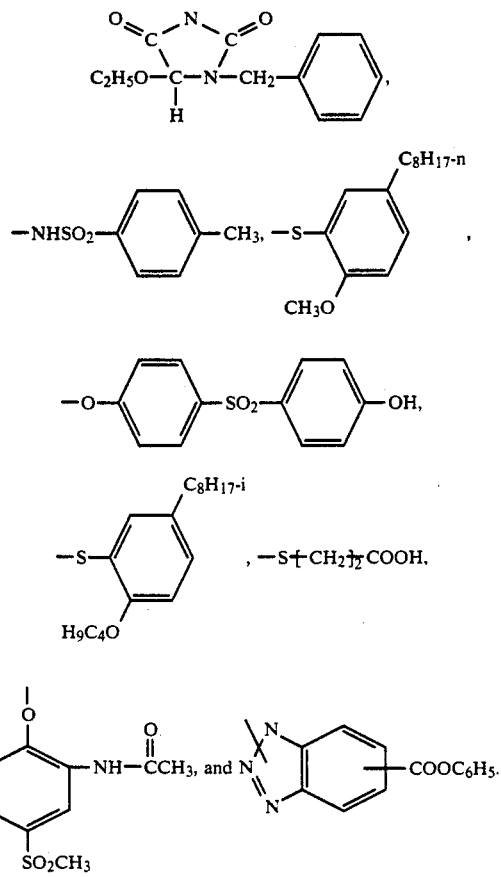

X as chlorine is especially advantageous for the method according to the present invention R and R' independently represent hydrogen or a coupler substituent known in the art which typically promotes solubility, diffusion resistance or dye hue or dye stability of the dye formed upon reaction of the coupler with the oxidized color developing agent.

Examples of such substituent groups include: an alkyl group which may be straight or branched, and which may be substituted, such as methyl, ethyl, n-propyl, n-butyl, t-butyl, trifluoromethyl, tridecyl or 3-(2,4-di-t-amylphenoxy) propyl; an alkoxy group which may be substituted, such as methoxy or ethoxy; an alkylthio group which may be substituted, such as methylthio or octylthio; an aryl group, an aryloxy group or an arylthio group, each of which may be substituted, such as phenyl, 4-t-butylphenyl, 2,4,6-trimethylphenyl, phenoxy, 2-methylphenoxy, phenylthio or 2-butoxy-5-t-octylphenylthio; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; cyano; an acyloxy group which may be substituted, such as acetoxy or hexadecanoyloxy; a carbamoyloxy group which may be substituted, such as N-phenylcarbamoyloxy or N-ethylcarbamoyloxy; a silyloxy group which may be substituted, such as trimethylsilyloxy; a sulfonyloxy group which may be substituted, such as dodecylsulfonyloxy; an acylamino group which may be substituted, such as acetamido or benzamido; an anilino group which may be substituted, such as phenylanilino or 2-chloroanilino; an ureido group which may be substituted, such as phenylureido or methylureido; an imido group which may be substituted, such as N-succinimido or 3-benzylhydantoinyl; a sulfamoylamino group which may be substituted, such as N,N-dipropylsulfamoylamino or N-methyl-N-decylsulfamoylamino.

Additional examples of substituent groups include: a carbamoylamino group which may be substituted, such as N-butylcarbamoylamino or N,N-dimethyl-carbamoylamino; an alkoxycarbonylamino group which may be substituted, such as methoxycarbonylamino or tetradecyloxycarbonylamino; an aryloxycarbonylamino group which may be substituted, such as phenoxycaronylamino or 2,4-di-t-butylphenoxycarbonylamino; a sulfonamido group which may be substituted, such as methanesulfonamido or hexadecanesulfonamido; a carbamoyl group which may be substituted, such as N-ethylcarbamoyl or N,N-dibutylcarbamoyl; an acyl group which may be substituted, such as acetyl or (2,4-di-t-amylphenoxy) acetyl; a sulfamoyl group which may be substituted such as N-ethylsulfamoyl or N,N-dipropylsulfamoyl; a sulfonyl group which may be substituted, such as methanesulfonyl or octanesulfonyl; a sulfinyl group which may be substituted, such as octanesulfinyl or dodecylsulfinyl; an alkoxycarbonyl group which may be substituted, such as methoxycarbonyl or butyloxycarbonyl; an aryloxycarbonyl group which may be substituted, such as phenyloxycarbonyl or 3-pentadecyloxycarbonyl; an alkenyl group carbon atoms which may be substituted; a carboxyl group which may be substituted; a sulfo group which may be substituted; hydroxyl; an amino group which may be substituted; or a carbonamido group which may be substituted.

Substituents for the above substituted R or R' groups include those that do not adversely affect the desired properties of the pyrazolotriazole coupler. Representative substituents for the substituted R or R' groups include: halogen, an alkyl group, an aryl group, an aryloxy group, a heterocyclic or a heterocyclic oxy group, cyano, an alkoxy group, an acyloxy group, a carbamoyloxy group, a silyloxy group, a sulfonyloxy group, an acylamino group, an anilino group, a ureido group, an imido group, a sulfonylamino group, a carbamoylamino group, an alkylthio group, an arylthio group, a heterocyclic thio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group, an aryloxycarbonyl group, an alkenyl group, a carboxyl group, a sulfo group, hydroxyl, an amino group or a carbonamido group.

Generally, the above groups and substituents thereof which contain an alkyl group may include an alkyl group having to 16 carbon atoms. The above groups and substituents thereof which contain an aryl group may include an aryl group having 6 to 8 carbon atoms, and the above groups and substituents which contain an alkenyl group may include an alkenyl group having 2 to 6 carbon atoms.

Preferably, R or R' represents hydrogen, an alkyl group, an aryl group, a carbonamido group, a sulfonamido group, a sulfone group, a thio group, a sulfoxide group, a ureido group or a multicyclic group.

Additionally, several of the above described R or R' groups constitute a ballast group, which is known in the photographic art as a radical of such size and configuration as to confer on the coupler molecule sufficient bulk to render the coupler substantially non-diffusible from the layer in which it is coated in a photographic element. Couplers of the invention may be attached to ballast groups, or to polymeric chains through one or more of the groups on the pyrazolotriazole nucleus. For example, one or more coupler moieties can be attached to the same ballast group. Representative ballast groups include substituted or unsubstituted alkyl, alkoxy, aryl or aryloxy groups containing 8 to 32 carbon atoms. Representative substituents include alkyl, aryl, alkoxy, aryloxy, alkylthio, arylthio, hydroxy, halogen, alkoxycarbonyl, aryloxycarbonyl, carboxy, acyl, acyloxy, carbonamido, carbamoyl, alkylsulfonyl, arylsulfonyl, sulfonamido, and sulfamoyl groups wherein the alkyl and aryl substituents and the alkyl and aryl portions of the alkoxy, aryloxy, alkylthio, arylthio, alkoxycarbonyl, arylcarbonyl, acyl, acyloxy, carbonamido, carbamoyl, alkylsulfonyl, arylsulfonyl, sulfonamido, and sulfamoyl substituents containing 1 to 30 carbon atoms and 6 to 30 carbon atoms, respectively, can be further substituted with such substituents.

Additionally, R or R' in formula (I) may constitute a reactive group which can be converted to a coupler substituent as defined above, thereby providing a dye-forming 1H-pyrazolo [1,5-b][2,4] triazole coupler. Thus, formula (I) includes compounds produced according to the method of the present invention which can then be further modified through the R or R' substituent to provide a desired dye-forming 1H-pyrazolo [1,5-b][2,4] triazole coupler by methods known in the art. For example, when R or R' is amino (—NH$_2$), the amine can be reacted with a group such as R"—CO—Cl, wherein R" is an alkyl, aryl, heterocyclic, alkoxy, aryloxy, alkylamino or arylamino group, to form a substituent of R"—CO—NH— on the pyrazolotriazole ring. An example of such a method is illustrated in U.S. Pat. No. 4,540,654, the disclosure of which is incorporated by reference.

Y and Z are independently substituent groups which have a Hammett sigma value of at least 0.05 ($\sigma_{m,p} \geq 0.05$). Preferably, each of Y and Z has a Hammett sigma value within the range of 0.060 to 0.800. Groups with these values can be readily determined by one of ordinary skill in the art (Journal of Medicinal Chemistry, Vol. 14, 680, 1971). Such groups provide a more efficient leaving group for the cyclization of compounds of formula (II). Suitable Y and Z groups include halogen, NO$_2$, and COOH and esters thereof. Preferably, the Y group is on the para position of the phenylene ring. Z represents a withdrawing group as defined for group Y, and, in addition, Z can also represent a lower alkyl group, such as methyl.

The following leaving groups are preferred, with the leaving groups listed in descending order of efficiency of the cyclization reaction.

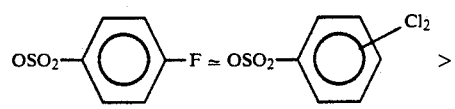

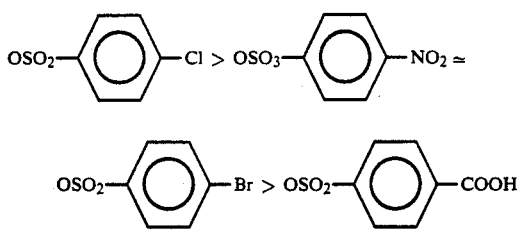

An illustrative overall reaction scheme follows. Compounds (II) and (IV) can be obtained by methods known in the art.

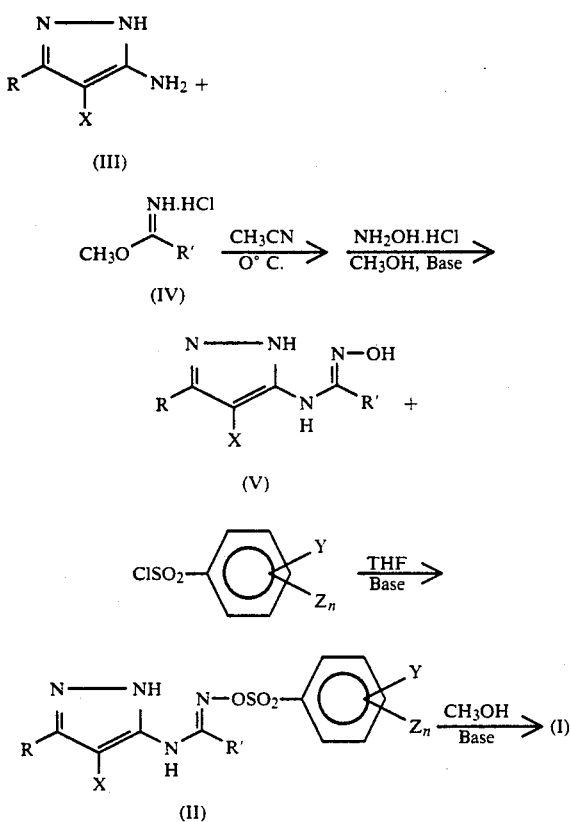

The preparation of the amidoxime of formula (V) from the aminopyrazole of formula (III) and the imidate of formula (IV) is preferably conducted in a solvent such as acetonitrile or a protic solvent (e.g., methanol, ethanol, propanol or isopropanol). While these solvents are preferred, other solvents which are inert with respect to the reactants and products and satisfactorily dissolve the subject materials can be employed. Examples of other suitable solvents are ether, tetrahydrofuran, dioxane, etc. Mild reaction temperatures, such as $-5°$ C. to $45°$ C., are employed with ambient pressure and a reaction time of 0.5 hour to 8 hours. A base is necessary for the step of formation of amidoxime of formula (V). Preferred bases are alkali metal salts of lower alcohols, such as sodium methoxide lithium methoxide, sodium ethoxide, etc.

The preparation of the intermediate of formula (II) is preferably carried out in an aprotic solvent such as tetrahydrofuran, dioxane, ethyl acetate or methyl acetate, e.g. Other solvents which are inert with respect to the reactants and products can be employed. The reaction is conducted in the presence of a base. Preferred bases include aromatic amines such as substituted or unsubstituted pyridine and tertiary amines such as trialkylamines. The amount of the base may be 0.5 to 2 equivalent, and preferably, 1 equivalent. The preferred reaction temperature is $-5°$ C. to $100°$ C., and the preferred reaction time is 1 to 10 hours.

The cyclization step leading to the compound of formula (I) from the key intermediate of formula (II) is preferably conducted in a protic solvent, such as the lower alcohols. Preferred alcohols include methanol, ethanol, propanol, isopropanol, etc. The cyclization is carried out in the presence of a base. The nature and the amount of the preferred bases are as previously defined for the preparation of the intermediate of formula (II). The preferred reaction temperature is $40°$ C. to $100°$ C., and the preferred reaction time is 1 to 15 hours.

Illustrative 1H-pyrazolo [1,5-b][1,2,4] triazole compounds of formula (I) which can be prepared according to the present invention are as follows. Each of the following compounds are useful as a dye-forming coupler in color photographic elements and processes. Each coupler contains a ballast group for R' in formula (I).

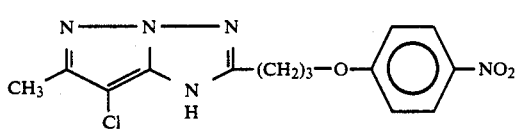

M-1

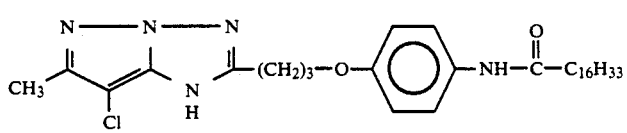

M-2

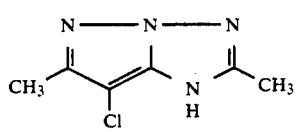

M-3

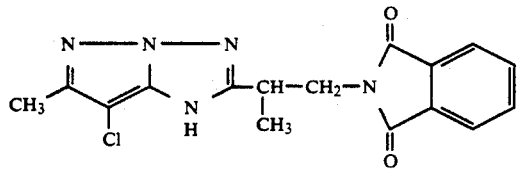
M-4
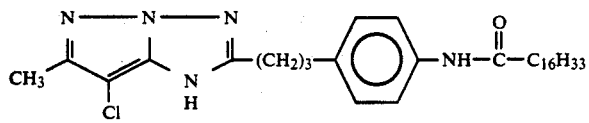
M-5
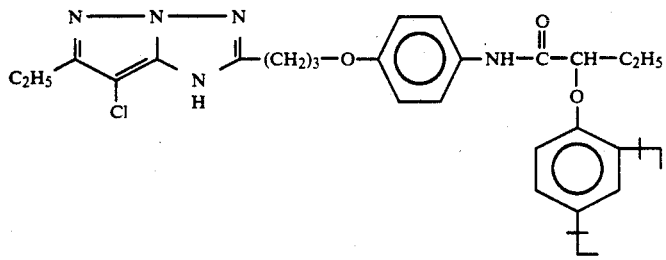
M-6
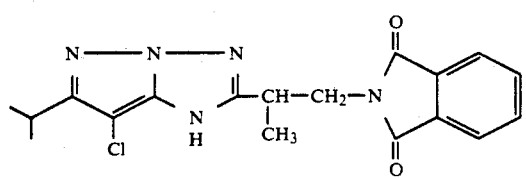
M-7
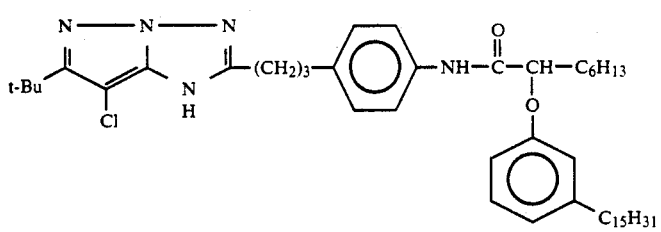
M-8
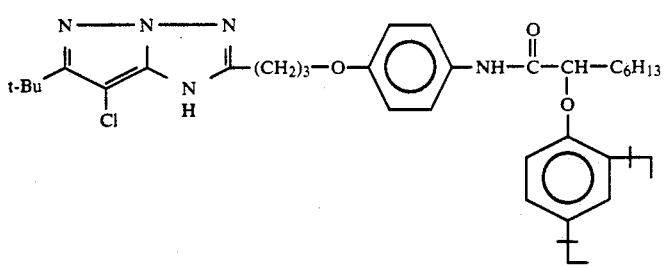
M-9
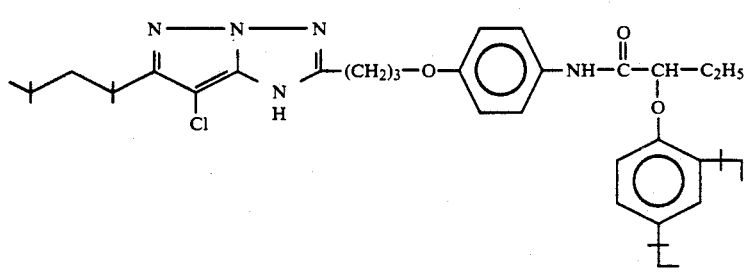
M-10

-continued
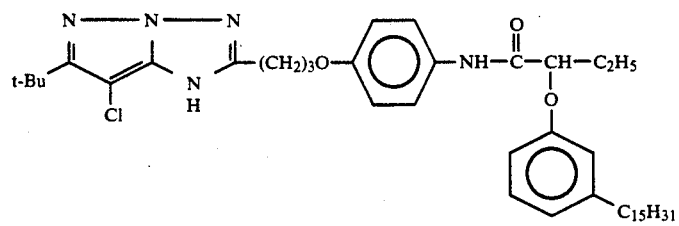 M-11
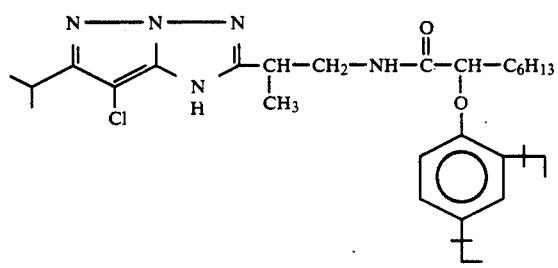 M-12
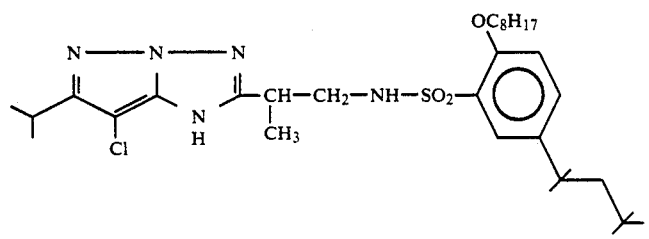 M-13
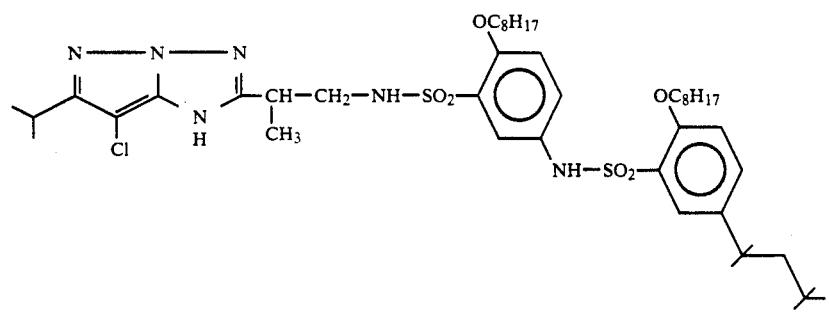 M-14
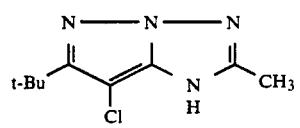 M-15
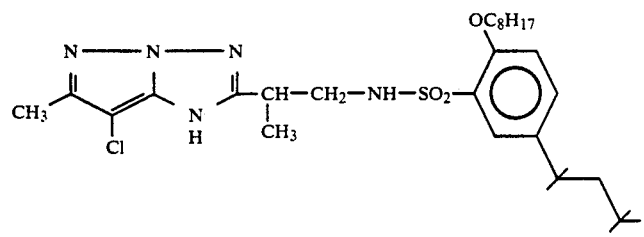 M-16

5,248,786

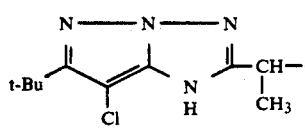
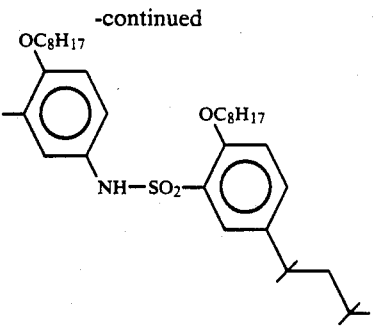

M-17

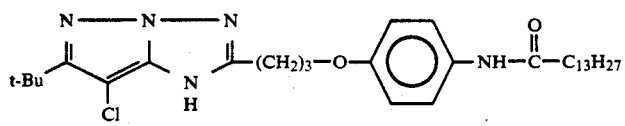

M-18

The following examples further illustrate the present invention, although it is understood that other compounds of formula (I) known in the art can be analogously prepared.

of sodium methoxide (25% w/w in methanol). The reaction was allowed to warm to room temperature and stirred overnight. The mixture was poured into 6.5 liters of an ice-water mixture. The mixture was stirred for 2 hours and the resulting solid was collected under suction, washed and dried in vacuo. The yield of the desired product (VA) was 285.40 g (86%). All the analytical data were in agreement with the structure.

Reaction Scheme

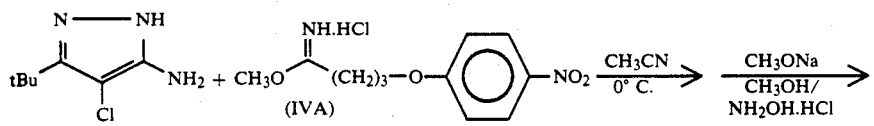

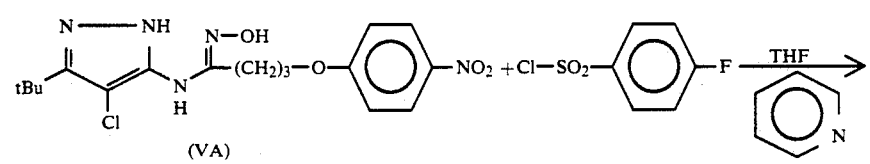

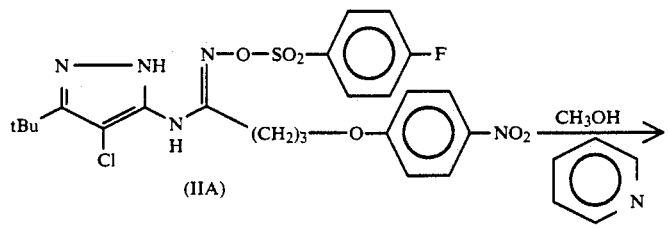

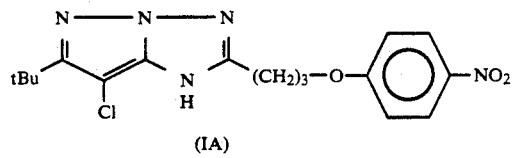

Preparation of Amidoxime (VA)

A suspension of 145 g (0.835 mol, 1.0 equiv) of 5-amino-3-tert-butyl-4-chloropyrazole (IIIA) in 1000 ml of acetonitrile was cooled to 0° C. followed by the portionwise addition of 240.75 g (0.876 mol, 1.05 equiv) of imidate (IVA). The reaction mixture was stirred at 0° C. for 3 hours. The mixture was concentrated in vacuo to yield a solid. To the solid, 1000 ml of methanol was added, followed by the addition of 63.79 g (0.918 mol, 1.10 equiv) of hydroxylamine hydrochloride. The stirred suspension was cooled to 0° C., followed by the poritonwise addition of 198.4 g (0.918 mol, 1.10 equiv)

Preparation of Coupler (IA)

To a solution of 3.95 g (0.010 mol, 1 equiv) of amidoxime (VA) in 35 ml of dried tetrahydrofuran at ambient temperature was added 0.95 g (0.012 mol, 1.2 equiv) of pyridine, followed by the addition of 2.14 g (0.010 mol, 1 equiv) of para-fluorobenzenesulfonylchloride.

The reaction mixture was stirred for 1 hour. At that time, no starting materials remained as evidenced by thin layer chromatography (TLC) analysis of the reaction mixture. The solvent was removed in vacuo. To the residue was added 35 ml of methanol, followed by the addition of 0.94 g (0.012 mol, 1.2 equiv) of pyridine. The reaction was heated at reflux for 2 hours. The cyclization was complete as observed by TLC. The reaction was cooled to 20° C. and poured into a mixture of ice water. The solid was collected, washed and dried under suction. The crude product was purified by trituration in 45 mL of methanol to yield 2.88 g (78%) of the desired coupler of formula (IA). All the analytical data were in agreement with the assigned structure.

The invention has been described in detail with particular reference to preferred embodiments thereof, but it will be understood that variations and modifications can be effected within the spirit and scope of the invention.

What is claimed is:

1. A compound of the formula:

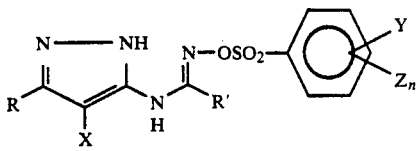

wherein Y is selected from the group consisting of halogen and nitro; R and R' are independently H or a coupler substituent; X is hydrogen or a coupling-off group; Z is a substituent group having a Hammett sigma value of 0.06 to 0.80; and n is 0, 1 or 2.

2. The compound of claim 1, wherein Y is in the para position on the phenylene ring and n is zero.

3. The compound of claim 2, wherein Y is F.

4. The compound of claim 2, wherein Y is Cl.

5. The compound of claim 2, wherein Y is $NO_2$.

6. The compound of claim 2, wherein Y is Br.

7. The compound of claim 2, wherein Y and Z are each Cl and n is 1.

8. The compound of claim 1, wherein X is Cl.

* * * * *